United States Patent [19]

Sharrock

[11] 4,368,730

[45] Jan. 18, 1983

[54] INTRAVENOUS CATHETER

[76] Inventor: Nigel Sharrock, 500 E. 85th St., New York, N.Y. 10028

[21] Appl. No.: 233,696

[22] Filed: Feb. 12, 1981

[51] Int. Cl.³ .......................... A61M 5/00; A61M 25/00
[52] U.S. Cl. ...................................... 604/158; 604/164; 604/282; 27/24 A
[58] Field of Search ................ 128/214.4, 348–350 R, 128/DIG. 16, DIG. 9, 654–658, 772; 27/24 A

[56] References Cited

U.S. PATENT DOCUMENTS

| | | | |
|---|---|---|---|
| 399,540 | 3/1889 | Lee | 128/349 R |
| 707,775 | 8/1902 | Harris | 128/349 R |
| 3,749,086 | 7/1973 | Kline | 128/772 |
| 3,757,768 | 9/1973 | Kline | 128/2 M |
| 3,841,308 | 10/1974 | Tate | 128/772 |
| 3,973,556 | 8/1976 | Fleischhacker et al. | 128/2 M |
| 4,020,829 | 5/1977 | Wilson et al. | 128/2 M |
| 4,033,331 | 7/1977 | Guss et al. | 128/2 M |
| 4,044,765 | 8/1977 | Kline | 128/214.4 |
| 4,068,660 | 1/1978 | Beck | 128/214.4 |

FOREIGN PATENT DOCUMENTS 43-27695  11/1968  Japan ............................ 128/DIG. 9

Primary Examiner—Dalton L. Truluck
Attorney, Agent, or Firm—Kenyon & Kenyon

[57] ABSTRACT

A stainless steel catheter assembly for communicating between a lumen of a blood vessel of a patient's body and a source or drain of fluid. A cannular termination is disposed at a distal portion of the catheter assembly and mechanically connected to respective distal ends of a wire-wound spring guide and a wire core which is disposed along an internal surface of the spring guide. A fitting for coupling to a source of intravenous fluid or a drainage device is disposed at a proximal portion of the catheter assembly and mechanically connected to the spring guide and wire core at respective proximal ends. Embodiments may be provided with a tapering distal termination which is disposed around a slidably retractable cannular needle for facilitating percutaneous access to the interior of a patient's vein. In other embodiments, the catheter assembly is terminated at the distal end in a blunted manner so as to permit the taking of central venous pressures. Such a bluntly terminated embodiment may be slidably disposed within a cannular needle for facilitating venipuncture.

8 Claims, 8 Drawing Figures

U.S. Patent    Jan. 18, 1983    Sheet 1 of 2    4,368,730
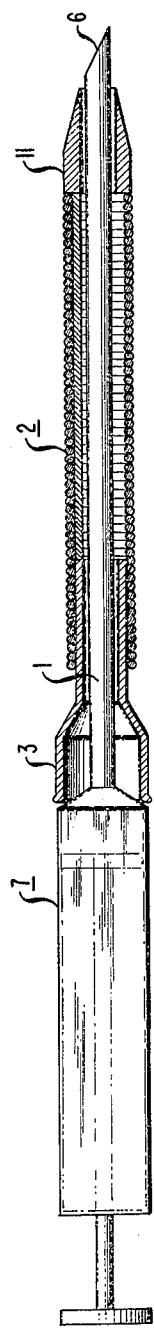
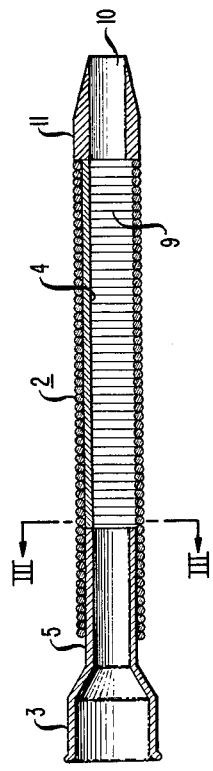
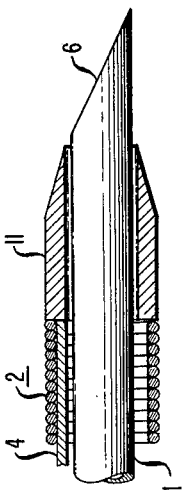
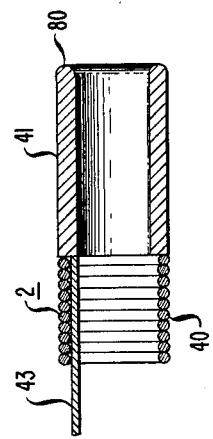
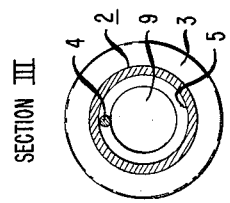

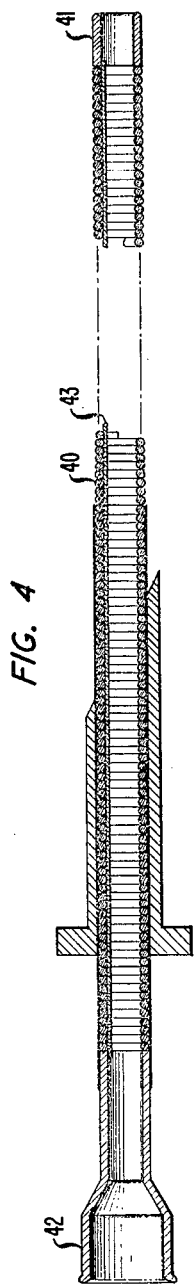
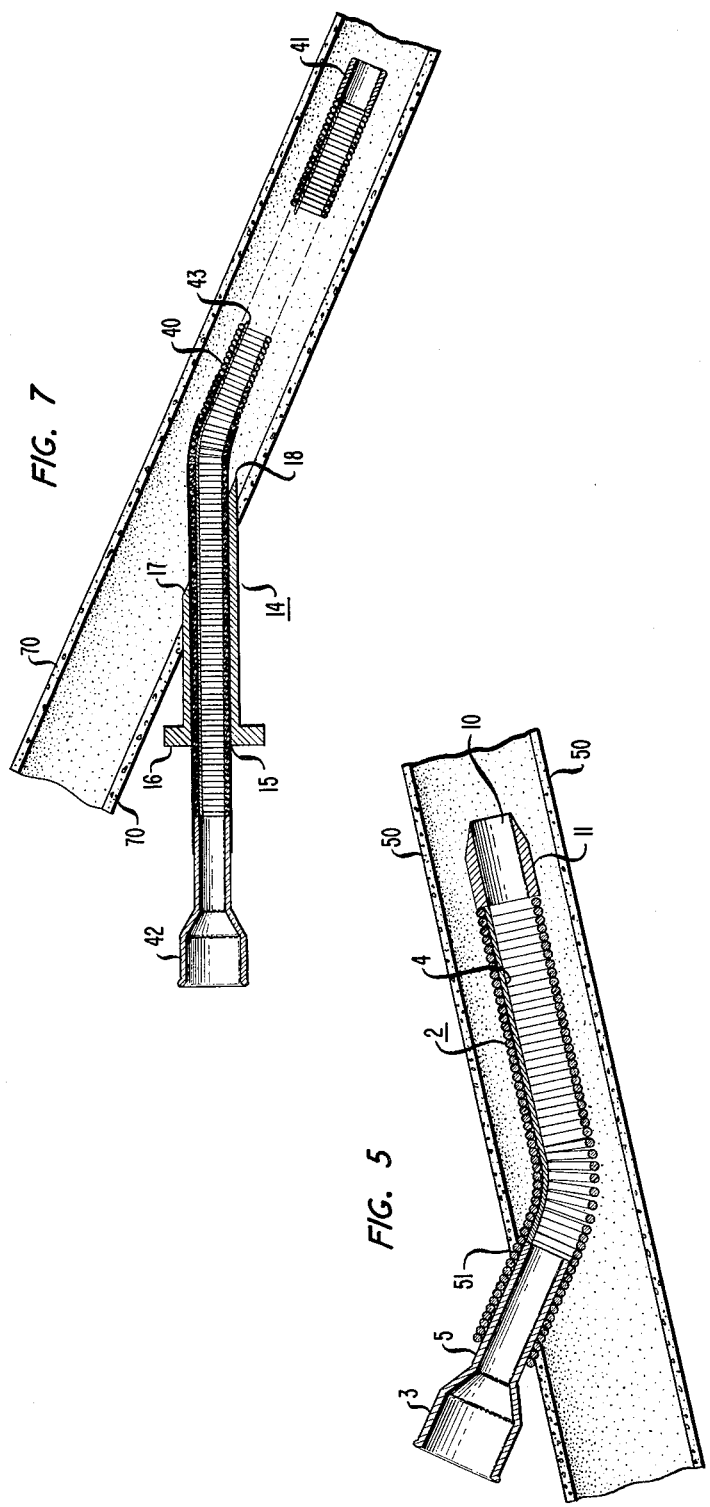
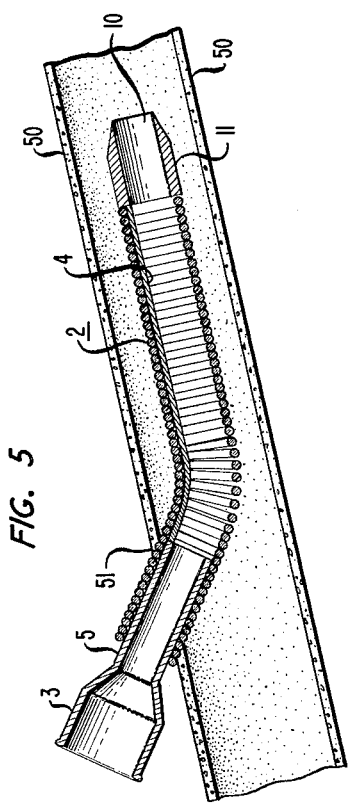
FIG. 4
FIG. 7
FIG. 5

INTRAVENOUS CATHETER

BACKGROUND OF THE INVENTION

This invention relates generally to devices for penetrating the lumen of a blood vessel of a patient and more particularly to improvements in catheter devices for coupling an intravenous fluid supply to a blood vessel, and for measuring central venous pressures.

Antiquated catheter devices formed from lengths of fragile glass, stainless steel, or plastic materials have created several problems. For example, continued use of plastic catheter devices in the body of a patient may cause reactions which lead to infections. Thus, medical practice requires that such plastic catheter devices be replaced often. Stainless steel devices avoided such adverse reactions, but were generally inflexible, thereby increasing the possibility of accidentally perforating the patient's blood vessels. To overcome these problems, sturdier and more flexible catheter devices formed of wire-wound coils have been proposed. Such helically wound cannular devices have enabled the construction of relatively long catheters which combine flexibility with the ability to transmit rotational torque so that the distal portion of the catheter which is disposed within a vessel of a patient can be guided by manipulation of the externally disposed proximal portion. Such maneuverability has permitted the insertion of catheter devices through vessels having curves of relatively short radii, while reducing the risk of damage to the wall of the vessel.

One helical coil spring guide which has been used in connection with the insertion of a catheter into the vessels of a body is shown in U.S. Pat. No. 3,973,556, which issued to Fleischhacker et al. Fleischhacker et al. teach a coil spring guide having a helically wound coil spring portion which, in operation, is disposed around a wire core. The wire core, which may be of stainless steel, is disposed near the longitudinal central axis of the coil spring, and is welded to the distal end of the coil spring. Another prior art spring guide and catheter combination is taught in U.S. Pat. No. 3,757,768 which issued to W. M. Kline. Kline teaches a manipulable unitary spring guide and catheter which is formed from a continuous, helically wound metal spring, and has a preconfigured wire stylette which aids in the guidance or positioning of the distal portion of the catheter. Thus, in addition to having a core wire which should preferably be removed to permit sufficient capacity within the lumen of the catheter for proper infusion of a fluid, or to permit the taking of pressure measurements, percutaneous access to the lumen of a vein or other vessel of a patient is achieved by the use of a sharpened needle through which the guide catheter is inserted, and which is thereafter immediately removed.

It is, therefore, an object of this invention to provide a flexible catheter which does not require the removal of a guide wire.

It is a further object of this invention to provide a catheter which can penetrate into, and remain for extended periods within, the lumen of a vessel of a patient's body without adversely interacting with the fluids therein and increasing the risk of infection.

It is a still further object of this invention to provide a catheter which is flexible and will not kink so as to minimize the possibility of accidentally perforating the wall of a patient's blood vessel or heart.

It is another object of this invention to provide a device for coupling a supply of intravenous fluid to a vessel of a patient's body almost immediately upon venipuncture.

SUMMARY OF THE INVENTION

The foregoing and other objects are achieved by this invention which provides a stainless steel catheter assembly having a flexible, wire-wound catheter with a core affixed therein. The core prevents the catheter from unwinding as the catheter enters and is maneuvered within a vessel or cavity of a patient.

In one embodiment of the invention, the wire-wound catheter and the core, which may also be made of stainless steel wire, are slidably disposed around the exterior of a cannular needle. At a distal end, the wire core is mechanically connected to a proximal end of a cannular termination which has a lumen through which passes the cannular needle. The wire core is mechanically connected at its proximal end to a distal portion of the coupling device, which may be formed of plastic or stainless steel. The coupling device is configured so as to receive, and provide a leakproof coupling with, a flexible I.V. tube for connecting a supply of fluid to the vessel of the patient, or, alternatively, a device for draining fluid from the vessel or a body cavity.

The cannular needle has a lumen which is internal to, and substantially axially aligned with, the lumen of the wire-wound spring guide. Since, as indicated, the wire core is disposed adjacent to an inner wall of the spring guide, the wire core does not obstruct or interfere with the insertion or extraction of the cannular needle, or with the flow of fluid through the lumen of the spring guide. The cannular needle may be of a type having a lumen which has a substantially constant radius with respect to a longitudinal central axis, and a tapering external radius so as to provide a relatively sharp edge at a terminating distalmost portion. Alternatively, the cannular needle may have a relatively constant external radius which is angularly terminated at the distal portion. Additionally, the cannular needle may couple with a syringe or other device for removing fluid samples from the patient.

In a second embodiment, the catheter assembly may be bluntly terminated at the distal end so as to be suitable for longer term placement in large veins, enable central venous pressure to be measured, and samples of venuous blood to be withdrawn, or permit intravenous feeding (hyperalimentation) to be infused. This embodiment is substantially longer in length than the above-described first embodiment, and enters a patient's blood vessel after venipuncture is achieved by a cannular needle having a sharpened distal point. However, the catheter enters the blood vessel through the lumen of the cannular needles, and accordingly does not surround the exterior of the cannular needle, as does the first embodiment. This insertion technique allows a relatively long catheter to enter the patient without unduly traumatizing the vessel wall at the point of catheter entry.

BRIEF DESCRIPTION OF THE DRAWINGS

Comprehension of the invention is facilitated by reading the following detailed description in conjunction with the drawings, in which:

FIG. 1 is a longitudinal section of a flexible helical coil catheter constructed in accordance with the principles of the invention, and is shown having an attached syringe for withdrawing blood samples;

FIG. 2 is a longitudinal section of a flexible helical coil catheter showing an internal support wire core and a leakproof section;

FIG. 3 is a cross-sectional representation of the embodiment of FIG. 2, taken orthogonal to a longitudinal central axis of the flexible helical coil catheter;

FIG. 4 is a longitudinal section of another embodiment of a flexible helical coil catheter which is elongated for use in a large or central vein;

FIG. 5 shows the manner in which the flexible helical coil catheter embodiment shown in FIG. 2 is disposed in use within a vein;

FIG. 6 is an enlarged cross-section of the distal end of the termination of the catheter embodiment of FIG. 2, for facilitating the penetration of a vein;

FIG. 7 shows the manner in which the elongated flexible helical coil catheter embodiment shown in FIG. 4 enters a large vein through a cannular needle; and FIG. 8 is an enlarged cross-sectional representation of a blunted distal termination for use with the catheter embodiment of FIG. 4.

DETAILED DESCRIPTION

FIG. 1 shows an embodiment of the invention wherein a cannular needle 1 is disposed within a flexible, wire-wound catheter assembly 2; the assembly being provided with a distal cannular termination 11 for facilitating the entry of the catheter assembly into a vein. In this embodiment, the needle protrudes beyond the distal termination by a small amount, illustratively approximately one millimeter. A hub-type fitting 3 is disposed at a proximal portion of the catheter assembly, and permits coupling to an external source of intravenous fluid after the cannular needle is removed. As shown, cannular needle 1 is coupled to a syringe device 7 for draining fluid from a vessel or body cavity of a patient. Coupling fitting 3 may be advantageously configured of a plastic material or stainless steel. Thus, a progressively tapered arrangement is provided between coupling fitting 3 and a distal, tapered point 6 of the cannular needle, which may be, for example, approximately six to eight centimeters in overall length.

FIG. 2 shows a magnified cross-sectional representation of wire-wound catheter assembly 2 and coupling device 3, without a needle or syringe. The figure shows a lumen 9 of the wire-wound cathether assembly 2 which is substantially in axial alignment with lumen 10 of cannular termination 11. A core 4 of stainless steel or other material is disposed in the interior of wire-wound catheter assembly 2, between cannular termination 11 with coupling fitting 3. Core 4 acts as a stiffening member for the flexible wire-wound coil assembly 2 so as to reinforce the helical coil assembly and prevent its unwinding.

In this embodiment, coupling fitting 3 is provided with an elongated tubular portion 5 which is at least partially disposed within helical coil 2. Core 4 is mechanically connected to tubular portion 5 at a distal portion thereof. The tubular portion is thereby maintained in position within helical coil 2 and provides a leak-proof section of helical coil near the coupling fitting.

FIG. 3 is a cross-sectional representation of the embodiment of FIG. 2, taken along cross-section plane III—III. The figure shows the cross-sectional shape of lumen 9 which is defined, in the portion of the catheter assembly near coupling fitting 3, by the cross-sections of elongated tubular section 5 and core 4. It should be noted that any of several known techniques may be used to connect the core to the coupling fitting or the distal termination which will control the degree of protrusion of core 4 into lumen 9.

FIG. 4 shows a cross-section of a second embodiment of the invention which may be substantially longer than the embodiment of FIG. 2, illustratively between approximately fifteen and ninety centimeters in overall length. A helical, wire-wound coil 40 is provided with a blunted distal termination 41 and a proximal end which has a coupling fitting 42. A core 43 is disposed within the helical coil and connected at its respective proximal and distal ends to coupling fitting 42 and blunted termination 41.

In this embodiment, the approximately six to nine centimeters of helical coil at the proximal end of the assembly near the coupling fitting may be provided with a plastic material, such as teflon or a silicon material, to prevent fluid leakages through the interstices of the helical coils. Since the leak-proof segment of this embodiment is substantially longer than that of the embodiment of FIG. 2, the use of a plastic material or silicone is preferable to the tubular extension of the coupling fitting described above with respect to the first embodiment because such a tubular extension would produce a relatively long and rigid leak-proof section which would be dangerous to use in flexible areas of the body of a patient, such as the elbows or the neck. However, the tubular extension leak-proofing technique would be suitable for catheters used in inflexible areas, such as the arm of a patient.

FIG. 5 shows the catheter assembly embodiment of FIG. 2 partially disposed within a vein 50. Sharpened portion 6 of cannular needle 1 in FIG. 1 enables penetration of the catheter into the vein through an opening 51 in FIG. 5. After such penetration, termination 11 is slid into the vein until the portion of the catheter which has been leak-proofed and made relatively rigid by tubular extension 5 traverses the venal opening 51. The remaining flexible portion of the catheter helical coil is prevented from unwinding by core 4 which is connected between tubular extension 5, and distal termination 11.

FIG. 6 shows core 4 connected to termination 11 so as not to interfere with the passage of cannular needle 1 therethrough. Termination 11 is tapered distally to facilitate venal penetration.

FIG. 7 shows a cannular needle 14 having a lumen 15 of substantially constant radius. Cannular needle 14 has a proximal end portion 16 and a sharpened distal end portion 17, which is of smaller outside radius than that of proximal portion 16. The cannular needle is terminated at its distal end in an angular configuration so as to produce a sharp edge 18. Cannular needle 14 slidably contains within its lumen 15 the wire-wound catheter assembly 40, through which is passed termination 41. The needle, by its edge 18, facilitates percutaneous access to the lumen of a vessel 70 of a patient. Once such access is achieved, wire-wound catheter 2 is slidably inserted through the cannular needle 14 into the lumen of the patient's vessel. Cannular needle 14 is retractably withdrawn from the patient's vessel after venipuncture and catheter insertion. The use of a cannular needle in this manner is especially advantageous when using catheter embodiments which are bluntly terminated so as to avoid inadvertent puncture of the vein or heart of the patient, and to facilitate measuring central venous pressures.

FIG. 8 shows the details of blunted distal termination 41 for the catheter assembly, which is usable for the measurement of central venous pressures. In this embodiment, termination 41 is provided with a blunted distal end 80 so as to prevent the inadvertent puncture of a vessel wall, or of the heart. As shown, termination 41 is mechanically connected to core 43 which is disposed within wire-wound catheter 40.

It is to be understood that this invention may be embodied to other specific forms without departing from the spirit or scope of the invention in the appended claims. The present embodiments are illustrative and not restrictive of the scope of the invention. For example, the devices described herein may be used to deliver fluid, such as cerebro-spinal fluid, into tissue spaces, such as the epidural space, pleural cavity, and others. Alternatively, the devices may be used to drain fluids from these or other cavities, wounds, or the peritoneal cavity.

What is claimed is:

1. An intravenous catheter assembly having a distal portion for insertion into the lumen of a vein of a patient and a proximal portion, the catheter assembly being CHARACTERIZED IN THAT there are provided:

cannular termination means formed of a metallic material and disposed on the distal portion of the catheter assembly, said cannular termination means having respective proximal and distal portions in axial alignment with each other to produce a substantially cylindrical lumen therethrough;

flexible cannular means having a distal end connected to said proximal portion of said termination means, said flexible cannular means being formed of helically wound wire so as to form a flexible lumen in axial alignment with said lumen of said cannular termination means;

fitting means disposed on the proximal portion of the catheter assembly, and having a respective distal portion for affording communication with a proximal portion of said flexible cannular means; and retention means disposed within said flexible cannular means, said retention means being mechanically connected at a distal end thereof to said proximal portion of said cannular termination means, and at a proximal end thereof to said distal portion of said fitting means for reinforcing said flexible cannular means along its length, between said cannular termination means and said fitting means.

2. The intravenous catheter assembly of claim 1 wherein said retention means comprises a wire core which is disposed adjacent to an inner surface of said flexible cannular means.

3. The intravenous catheter assembly of claim 2 wherein said cannular termination means has a longitudinal central axis; said
proximal portion has a first predetermined axial length along said longitudinal central axis, a predetermined external radius with respect to said longitudinal central axis, and an internal substantially cylindrical wall defining said lumen and arranged at a predetermined internal radius with respect to said longitudinal central axis; and
said tapering distal portion has a second predetermined axial length along said longitudinal central axis adjacent to said first predetermined axial length, said tapering distal portion having a tapering external radius with respect to said longitudinal central axis, said tapering external radius continuously reducing in length distally with respect to said longitudinal central axis along said second predetermined axial length so as to produce a sharpened edge at a distal most portion of said cannular termination means, said tapering distal portion having an internal wall defining said lumen having said predetermined internal radius with respect to said longitudinal central axis.

4. The intravenous catheter assembly as claim 3 wherein there is further provided cannular needle means having a cylindrical body having a predetermined external radius which is smaller than said predetermined internal radius of said lumen of said cannular termination means, said cannular needle means being slidably disposed within said lumen of said cannular termination means.

5. An intravenous catheter assembly according to claim 2 wherein said cannular termination means has a longitudinal central axis, said proximal portion of said cannular termination means for mechanically coupling with said flexible cannular means and said retention means having a predetermined external radius with respect to said longitudinal central axis and an internal wall defining a lumen having a predetermined internal radius with respect to said longitudinal central axis, and said distal portion having a beaded edge disposed around a distal opening of said cannular termination means for communicating between said lumen of said proximal portion and a lumen of a vein of the patient.

6. The intravenous catheter assembly of claim 5 wherein said catheter assembly is slidably disposed within a cannular needle means, said cannular needle means having a longitudinal central axis and a substantially cylindrical internal wall defining a lumen having a predetermined internal radius with respect to said longitudinal central axis, said predetermined internal radius being larger than said predetermined external radius of said cannular termination, a proximal portion having a first predetermined length parallel to said longitudinal central axis, said proximal portion having a first predetermined external radius with respect to said longitudinal central axis, and a distal portion having a second predetermined length parallel to said longitudinal central axis, said distal portion having a second predetermined external radius with respect to said longitudinal central axis, said second predetermined external radius being shorter than said first predetermined external radius, said distal portion being adjacent to said proximal portion and angularly terminated at a distalmost end, said angular termination being at an angle which is less than orthogonal with respect to said longitudinal central axis, for providing a sharpened distalmost edge which facilitates venipuncture so as to provide communication between said lumen of said cannular needle means and a lumen of the vein of the patient.

7. The intravenous catheter assembly of claim 1 wherein said fitting means is adapted for receiving and coupling to an I.V. supply.

8. The intravenous catheter assembly of claim 1 wherein said fitting means is adapted for receiving and coupling to a device for removing fluid from the body of the patient.

* * * * *